US012673203B2

(12) United States Patent
Zhou et al.

(10) Patent No.: US 12,673,203 B2
(45) Date of Patent: Jul. 7, 2026

(54) STIMULATOR CIRCUIT, A SYSTEM FOR PROVIDING STIMULATION OF A BRAIN AND/OR NERVE AND A METHOD FOR PROVIDING A COMPENSATED STIMULATION SIGNAL

(71) Applicant: Stichting IMEC Nederland, Eindhoven (NL)

(72) Inventors: Meiyi Zhou, Eindhoven (NL); Haoming Xin, Eindhoven (NL); Roland Van Wegberg, Oss (NL)

(73) Assignee: STICHTING IMEC NEDERLAND, Eindhoven (NL)

( * ) Notice: Subject to any disclaimer, the term of this patent is extended or adjusted under 35 U.S.C. 154(b) by 273 days.

(21) Appl. No.: 18/511,762

(22) Filed: Nov. 16, 2023

(65) Prior Publication Data

US 2024/0189593 A1     Jun. 13, 2024

(30) Foreign Application Priority Data

Dec. 7, 2022     (EP) .................................... 22211971

(51) Int. Cl.
*A61N 1/36*          (2006.01)
*A61N 1/04*          (2006.01)
*A61N 1/20*          (2006.01)

(52) U.S. Cl.
CPC ..... *A61N 1/36034* (2017.08); *A61N 1/36025* (2013.01); *A61N 1/0456* (2013.01); *A61N 1/20* (2013.01)

(58) Field of Classification Search
CPC ........... A61N 1/36034; A61N 1/36025; A61N 1/0456; A61N 1/20; A61N 1/36142;
(Continued)

(56) References Cited

U.S. PATENT DOCUMENTS 9,566,449 B2 *   2/2017   Perryman ............ A61N 1/3787
2016/0354612 A1 *  12/2016   Butz ................... A61N 1/3782
(Continued)

OTHER PUBLICATIONS

Aristovich et al: "Model-based geometrical optimisation and in vivo validation of a spatially selective multielectrode cuff array for vagus nerve neuromodulation", Journal of Neuroscience Methods, 109079, pp. 1-13, 2021.
(Continued)

*Primary Examiner* — Mallika D Fairchild
(74) *Attorney, Agent, or Firm* — MOSER TABOADA

(57) ABSTRACT
A stimulator circuit comprises: a stimulation signal generating unit configured to generate a stimulation signal and provide the stimulation signal to an output wherein the stimulation signal is an alternating current, AC, signal having a sinusoidal-like waveform; and a compensation unit configured to generate a compensation current signal, wherein the compensation unit comprises a common mode voltage monitoring element configured to monitor a common mode voltage based on the stimulation signal, and a charge balancing element configured to generate the compensation current signal based on the common mode voltage; wherein the compensation unit is configured to provide the compensation current signal to the output for compensating an unbalanced charge of the stimulation signal and forming a compensated stimulation signal at the output.

14 Claims, 4 Drawing Sheets

(58) Field of Classification Search
    CPC ................ A61N 1/36014; A61N 1/323; A61N
                                    1/36157; A61N 1/08
    See application file for complete search history.

(56)                    References Cited

U.S. PATENT DOCUMENTS

| 2017/0216594 | A1* | 8/2017 | Grossman | ............ A61N 1/0529 |
| 2019/0091470 | A1 | 3/2019 | Lee et al. | |
| 2020/0179698 | A1 | 6/2020 | Schepis et al. | |
| 2022/0023629 | A1* | 1/2022 | Claude | .............. A61N 1/36082 |

OTHER PUBLICATIONS

Grossman et al: "Noninvasive Deep Brain Stimulation via Tempo-rally Interfering Electric Fields", Cell, 169, pp. 1029-1041, 2017.
Merrill et al: "Electrical stimulation of excitable tissue: design of efficacious and safe protocols", Journal of Neuroscience Methods, 141, pp. 171-198, 2005.
Pu et al: "A CMOS Dual-Mode Brain-Computer Interface Chipset With 2-mV Precision Time-Based Charge Balancing and Stimulation-Side Artifact Suppression", IEEE Journal of Solid-State Circuits, vol. 57, No. 6, pp. 1824-1840, 2022.
Ortmanns et al: "A 232-Channel Epiretinal Stimulator ASIC", IEEE Journal of Solid-State Circuits, vol. 42, No. 12, pp. 2946-2959, 2007.
Noorsal et al: "A Neural Stimulator Frontend With High-Voltage Compliance and Programmable Pulse Shape for Epiretinal Implants", IEEE Journal of Solid-State Circuits, vol. 47, No. 1, pp. 244-256, 2012.
European Search Report in European Patent Application No. 22211971.1 dated May 15, 2023.

* cited by examiner

STIMULATOR CIRCUIT, A SYSTEM FOR PROVIDING STIMULATION OF A BRAIN AND/OR NERVE AND A METHOD FOR PROVIDING A COMPENSATED STIMULATION SIGNAL

CROSS-REFERENCE TO RELATED APPLICATIONS

The present application claims the benefit of and priority to EP Patent Application Serial No. 22211971.1, filed Dec. 7, 2022, the entire contents of which is incorporated herein by reference.

TECHNICAL FIELD

The present description relates to a stimulator circuit. The present description particularly relates to a stimulator circuit which may be used in a system for providing stimulation to a brain and/or a nerve. The present description also relates to a method that may be performed in a stimulator circuit.

BACKGROUND

Electrical stimulation is widely used in clinical practice. Stimulation may typically be delivered using biphasic charge balanced pulses.

When an accurate spatial selectivity of stimulation is desired, interferential stimulation based on two or more stimulation signals may be used. Interference of the two or more stimulation signals may thus generate an interferential stimulation signal within tissue, which allows selectively stimulating a location within the tissue.

However, the stimulation signals for forming the interferential stimulation may be continuously provided for a long period of time. There is a need to ensure charge balancing in order to avoid safety issues in relation to electrodes and/or tissue.

SUMMARY

An objective of the present description is to ensure charge balancing in stimulation that is to be provided to a subject.

This and other objectives are at least partly met by the invention as defined in the independent claims. Preferred embodiments are set out in the dependent claims.

According to a first aspect, there is provided a stimulator circuit, said stimulator circuit comprising: a stimulation signal generating unit configured to generate a stimulation signal and provide the stimulation signal to an output, wherein the stimulation signal is an alternating current (AC) signal having a sinusoidal-like waveform; and a compensation unit configured to generate a compensation current signal, wherein the compensation unit comprises a common mode voltage monitoring element configured to monitor a common mode voltage based on the stimulation signal, and a charge balancing element configured to generate the compensation current signal based on the common mode voltage; wherein the compensation unit is configured to provide the compensation current signal to the output for compensating an unbalanced charge of the stimulation signal and forming a compensated stimulation signal at the output.

A mismatch between positive and negative parts of a waveform may cause an unbalanced charge to electrodes connected to the stimulator circuit. The unbalanced charge may introduce an offset voltage build-up onto the electrodes over time, in particular as an interface between electrode and tissue is often very capacitive. If the stimulator circuit is used continuously for a long period of time, the unbalanced charge can cause safety issues to the electrode and/or the tissue. For instance, the offset voltage build-up may form such a large electrical field that electrical breakdown of water occurs. The offset voltage build-up may also cause the electrode to break such that a subject to the stimulation may be exposed to toxic substances.

Thanks to the compensation current signal provided by the stimulator circuit, any unbalance charge may be compensated during stimulation by the stimulation signal. Thus, the stimulator circuit may allow the stimulation signal to be output continuously for a long period of time without any need to interrupt stimulation in order for charge balance compensation to be performed.

Thanks to the stimulator circuit, a compensation unit is used for compensating an unbalanced charge of the stimulation signal. The stimulator circuit may thus ensure that charge balancing is provided so as to compensate for any mismatch between positive and negative parts of the waveform of the stimulation signal. This implies that the stimulator circuit may provide compensation instead of (or in combination with) control of functionality of components of the stimulator circuit.

The stimulation signal generating unit may comprise components having nonideal function which may cause an unbalance in the waveform. If the stimulation signal generating unit is to be provided in an integrated circuit, compensation of nonideal function of components may be difficult or impossible to achieve in the integrated circuit. Thanks to providing the compensation unit, the stimulator circuit may still ensure that an unbalanced charge is compensated to improve safety of the stimulator circuit. Hence, the stimulator circuit may be provided in an integrated circuit providing a very small form factor of the stimulator circuit.

The AC signal having a sinusoidal-like waveform implies that the AC signal may be sinusoidal but does not necessarily need to be a pure sinusoidal waveform. For instance, the AC signal may be a pseudo-sinusoidal waveform, a modified sinusoidal waveform, or a multi-level waveform approximating a sinusoidal waveform.

The stimulation signal generating unit may output a current signal. The current signal may be converted to a voltage signal by being output to an electrode connected to tissue. Thus, the compensation unit may be configured to monitor a common mode voltage based on a stimulation signal which may be a current signal. The compensation unit may further output a compensation current signal that compensates an unbalanced charge of the stimulation current signal.

The common mode voltage monitoring may be provided by a low pas filter. However, the common mode voltage may change slowly in relation to a frequency of the stimulation signal, where the change of the common mode voltage may be based on a small unbalance between positive and negative parts of the waveform. Thus, if a low pass filter is to be used, the filtering may need to use a low cut-off frequency which can require a large circuit area.

According to an embodiment, the common mode voltage monitoring element is configured to perform extreme point detection of the stimulation signal for determining an unbalance of the common mode voltage based on the stimulation signal.

This implies that the common mode voltage may be detected using a circuit which may not require a large area. Thus, the stimulator circuit may be compact.

The common mode voltage monitoring element may be configured to detect a maximum and/or a minimum of the stimulation signal. The common mode voltage monitoring element may use the extreme point detection, such that at beginning of compensation a trend of the common mode voltage is monitored, which may be used for generating the compensation current signal.

According to an embodiment, the common mode voltage monitoring element comprises a maximum point detection element for detecting local maxima of the stimulation signal, a minimum point detection element for detecting local minima of the stimulation signal, and an averaging element for determining an average based on detected local maxima and detected local minima for monitoring the common mode voltage.

Thus, the common mode voltage monitoring element may determine the common mode voltage as the average of detected local maxima and minima. This implies that the common mode voltage monitoring element may accurately determine the common mode voltage.

According to an embodiment, the compensation unit comprises an attenuator configured to attenuate the stimulation signal, and wherein the common mode voltage monitoring element is configured to monitor the common mode voltage based on an attenuated stimulation signal received from the attenuator.

An output signal swing at an electrode receiving the stimulator signal may be large, at least for particular applications, such as when the stimulator circuit is used for peripheral nerve stimulation.

Thanks to the compensation unit comprising the attenuator, the compensation unit may provide the compensation current signal in a power-efficient manner. Thanks to the stimulation signal being attenuated, the common mode voltage monitoring element is not exposed to large voltage swings, such that power consumption of the common mode voltage monitoring element may be limited.

The compensation unit may further be configured to initially generate a feedback current based on the attenuated stimulation signal such that the generation of the feedback current may be performed in a power efficient manner.

According to an embodiment, the compensation unit further comprises a transconductance amplifier for generating a feedback current based on comparing the common mode voltage to a reference voltage.

The feedback current may be used for generating the compensation current signal to be output by the compensation unit. The transconductance amplifier may be configured to convert a determined common mode voltage into a feedback current.

The transconductance amplifier may need a high transconductance in order for the compensation unit to provide good compensation. Thus, power consumption of the transconductance amplifier may be relatively large and the transconductance amplifier advantageously determines the feedback current based on the attenuated stimulation signal. This implies that the transconductance amplifier may use a low voltage supply in order for power consumption to be limited.

As used herein, the term "low voltage" may refer to a voltage suitable for typical use with integrated circuits. Thus, a low voltage may be a voltage smaller than 5 V, such as smaller than 3.5 V. Correspondingly, a voltage larger than 5 V may be referred to herein as a "high voltage".

According to an embodiment, the compensation unit further comprises a current output stage configured to amplify the feedback current for forming the compensation current signal.

Thus, the compensation unit may be configured to generate the compensation current signal via the current output stage. The current output stage may be implemented with a high voltage supply and may provide a high output impedance. This implies that the current output stage may be compatible with large output signal swings of the stimulator circuit.

According to an embodiment, the compensation unit is configured to be duty cycled.

This implies that the compensation unit may not be continuously operating during output of a stimulation signal by the stimulator circuit. Hence, power consumption of the stimulator circuit may be reduced, by the compensation unit being intermittently turned off.

The compensation unit may thus be configured to output a compensation current signal at discrete time periods while a stimulation signal is continuously output by the stimulator circuit.

The compensation unit may be configured to be duty cycled so as to be active during the discrete time periods and be inactive or turned off during time intervals between the discrete time periods. The time intervals of the compensation unit being inactive may be set such that a risk of a too large offset voltage being built up during the time intervals is avoided.

The duty cycle may be dynamically controlled in dependence of characteristics of the stimulation signal. Thus, if the stimulation signal generating unit generates a well-balanced waveform, the duty cycle of the compensation unit may be set to be low.

According to an embodiment, the compensation current signal is a direct current (DC) signal.

When a compensation loop formed by the compensation unit is stable, the compensation current signal will be a DC signal. This implies that the compensation current signal will not affect performance of the AC stimulation signal output by the stimulator circuit and will thus not affect a stimulation of a living being. For instance, if stimulation of a living being is to be performed by interferential stimulation, the DC signal provided by the compensation current signal will have no effect on the interferential stimulation.

According to an embodiment, the stimulation signal generating unit comprises a current source and a current sink for generating the AC stimulation signal, wherein the current source and the current sink are independent components.

Thanks to using independent components of the current source and the current sink, cross-talk between two stimulator circuits, which may be used for example in interferential stimulation, may be avoided during stimulation.

However, using independent components, there is a higher risk for an unbalanced charge being provided by the waveform of the stimulation signal, since the current source and the current sink may exhibit different nonideal characteristics.

Hence, the stimulator circuit providing a compensation of an unbalanced charge of the stimulation signal may be particularly useful when the current source and the current sink are independent components.

According to a second aspect, there is provided a system for providing stimulation of a brain and/or a nerve of a living being, said system comprising: the stimulator circuit according to the first aspect; and at least one electrode connected to the stimulator circuit for receiving the compensated stimulation signal from the output of the stimulator circuit, wherein the at least one electrode is configured to be arranged in relation to the brain and/or the nerve for transmitting the compensated stimulation signal into the brain and/or the nerve.

Effects and features of this second aspect are largely analogous to those described above in connection with the first aspect. Embodiments mentioned in relation to the first aspect are largely compatible with the second aspect.

Thus, the stimulator circuit may be part of a system for providing stimulation of a brain and/or a nerve of a living being, such as a human being or an animal. The stimulator circuit may thus provide the compensated stimulation signal to an electrode located for transmitting the compensated stimulation signal to the living being. The stimulator circuit may be used in any application where an AC stimulation signal is to be provided to the living being.

The compensated stimulation signal may be transmitted into the brain and/or a nerve based on one electrode connected to the stimulator circuit and a reference electrode. The reference electrode may be a common reference electrode shared by a plurality of stimulator circuits.

The compensated stimulation signal may alternatively be provided by the stimulator circuit to a pair of electrodes for transmitting the compensated stimulation signal into the brain and/or nerve.

According to a third aspect, there is provided a system for providing temporal interference stimulation of a brain and/or a nerve of a living being, said system comprising: a first stimulator circuit according to the first aspect for forming a first compensated stimulation signal at the output of the first stimulator circuit; at least one first electrode connected to the first stimulator circuit for receiving the first compensated stimulation signal from the output of the first stimulator circuit, wherein the at least one first electrode is configured to be arranged in a first relation to the brain and/or the nerve for transmitting the first compensated stimulation signal into the brain and/or the nerve; a second stimulator circuit according to the first aspect for forming a second compensated stimulation signal at the output of the second stimulator circuit; and at least one second electrode connected to the second stimulator circuit for receiving the second compensated stimulation signal from the output of the second stimulator circuit, wherein the at least one second electrode is configured to be arranged in a second relation to the brain and/or the nerve for transmitting the second compensated stimulation signal into the brain and/or the nerve; wherein the at least one first electrode and the at least one second electrode are configured to be arranged in relation to the brain and/or the nerve for forming an interferential stimulation signal in the brain and/or the nerve based on interference between the first compensated stimulation signal and the second compensated stimulation signal.

Effects and features of this third aspect are largely analogous to those described above in connection with the first and second aspects. Embodiments mentioned in relation to the first and second aspects are largely compatible with the third aspect.

Thus, a system for temporal interference stimulation may comprise at least two stimulator circuits for generating at least a first and a second compensated stimulation signal to be used for forming the interferential stimulation signal.

Each stimulator circuit may generate a compensated stimulation signal that is continuously output for a long period of time in order to generate the interferential stimulation signal based on interference of the compensated stimulation signals. The system therefore advantageously makes use of the stimulator circuit according to the first aspect for each of the stimulator circuits of the system, to ensure that build-up of offset voltage at the electrodes is avoided.

Each stimulator circuit may be associated with a respective electrode. As discussed above for the second aspect, the compensated stimulation signal may be output to a single electrode, wherein a reference electrode may further be used, which reference electrode may be common to two or more stimulator circuits. Alternatively, the compensated stimulation signal may be output to a pair of electrodes, wherein each stimulator circuit is associated with a respective pair of electrodes.

As yet another alternative, a first and a second pair of stimulator circuits may be used for output of stimulation signals to a first and a second pair of electrodes. The first stimulator circuit may thus be combined with a third stimulator circuit to form the first pair of stimulator circuits and the second stimulator circuit may be combined with a fourth stimulator circuit to form the second pair of stimulator circuits. The first stimulator circuit and the third stimulator circuit may comprise voltage-controlled current sources configured to receive an identical voltage waveform. For the first stimulator circuit the voltage waveform may be provided at a positive input of the voltage-controlled current source with a negative input grounded. For the third stimulator circuit the voltage waveform may be provided at a negative input of the voltage-controlled current source with a positive input grounded. Each of the first stimulator circuit and the third stimulator circuit may be connected to a respective electrode of the first pair of electrodes which may thus receive compensated stimulation signals that are in anti-phase for forming a stimulation signal to be transmitted into the brain and/or the nerve.

It should further be realized that the stimulator circuit may be connected to a set of electrodes, such that the electrode to be used for transmitting of the compensated stimulation signal into the brain and/or nerve may be dynamically selected when the system is used.

It should be realized that the system may comprise more than two stimulator circuits for output of more than two compensated stimulation signals. A number of stimulator circuits of the system may be dependent on the stimulation to be provided. For instance, in some embodiments, the system may comprise more than two stimulator circuits for generating more than two compensated stimulation signals for causing an interferential stimulation signal to be formed based on more than two compensated stimulation signals.

According to a fourth aspect, there is provided a method for providing a compensated stimulation signal, said method comprising: generating a stimulation signal and providing the stimulation signal to an output, wherein the stimulation signal is an alternating current (AC) signal having a sinusoidal-like waveform; monitoring a common mode voltage based on the stimulation signal; generating a compensation current signal based on the common mode voltage and providing the compensation current signal to the output for compensating an unbalanced charge of the stimulation signal and forming the compensated stimulation signal at the output.

In particular, the method may be performed in the stimulator circuit of the first aspect or in the system according to the second or third aspects.

Effects and features of this fourth aspect are largely analogous to those described above in connection with the first, second, and third aspects. Embodiments mentioned in relation to the first, second, and third aspects are largely compatible with the fourth aspect.

Thanks to the method, a compensated stimulation signal may be provided to avoid build-up an offset voltage at an electrode.

BRIEF DESCRIPTION OF THE DRAWINGS

The above, as well as additional objects, features, and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
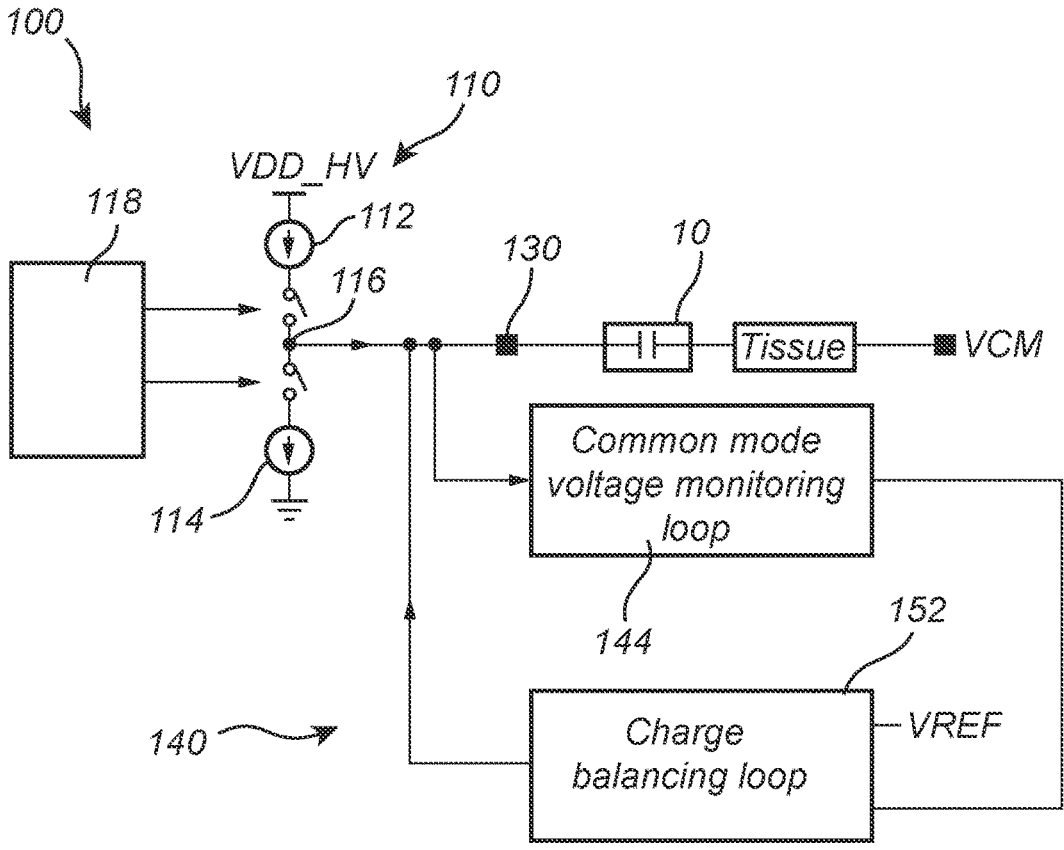
FIG. 1 is a schematic view of a stimulator circuit according to a first embodiment.

Referring now to FIG. 1, a stimulator circuit 100 according to a first embodiment will be described.

The stimulator circuit 100 comprises a stimulation generating unit 110 configured to generate a stimulation signal. The stimulation generating unit 110 may comprise a current source 112 and a current sink 114. The current source 112 may be connected between a supply voltage and an output node 116 and the current sink 114 may be connected between ground and the output node 116.

The stimulation generating unit 110 may further comprise a control unit 118 which may provide digital control of a first switch 120 arranged between the current source 112 and the output node 116 and a second switch 122 arranged between the current sink 114 and the output node 116. The control unit 118 may thus control which of the current source 112 and the current sink 114 is connected to the output node 116.

The current source 112 and the current sink 114 may thus form independent components for generating an AC stimulation signal at the output node 116. The use of independent components may avoid cross-talk between two stimulator circuits, which may be used for example for providing interferential stimulation, during output of a stimulation signal at the output node 116.

The output node 116 may further be connected to an output 130 of the stimulator circuit 100. The output 130 may further be connected, e.g., to an electrode for providing the stimulation signal to a living being. It should be realized that the electrode 10 may not necessarily be part of the stimulator circuit 100.

The stimulation signal generating unit 110 may be configured to output the stimulation signal at the output node 116. The stimulation signal may be an AC signal having a sinusoidal-like waveform, such as a pure sinusoidal waveform, a pseudo-sinusoidal waveform, a modified sinusoidal waveform, or a multi-level waveform approximating a sinusoidal waveform.

Figure 2:
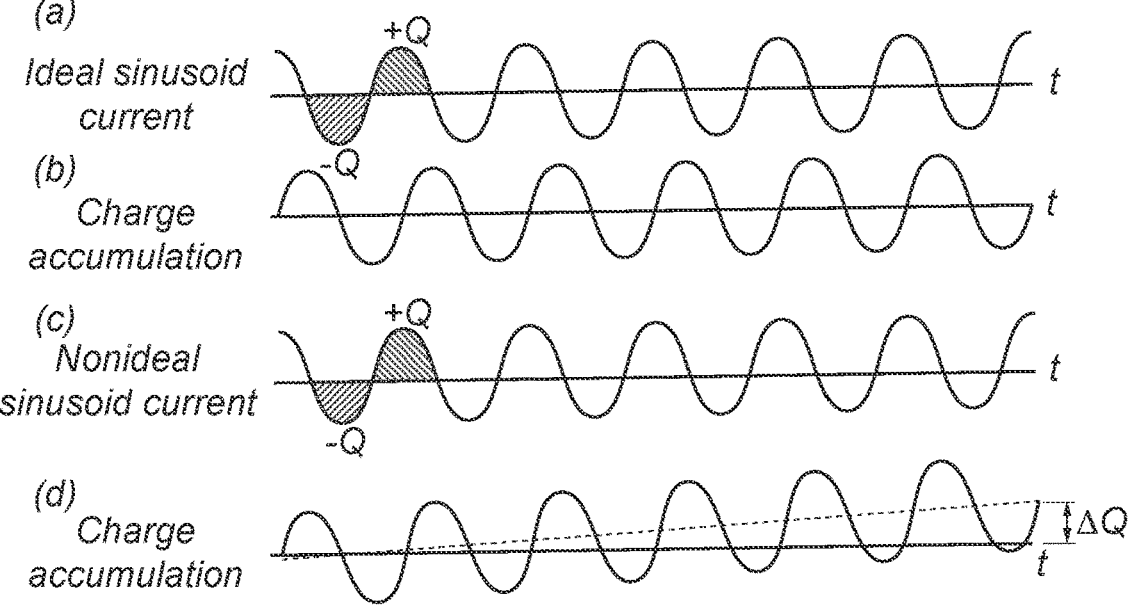
FIG. 2 shows charts illustrating an unbalanced charge provided to an output.

The stimulator circuit 100 may further comprise a compensation unit 130 configured to provide a compensation current signal to an output of the stimulator Referring now to FIG. 2, charge accumulation at an electrode 10 connected to the output 130 of the stimulator circuit 100 is illustrated. FIG. 2 shows in chart (a) an ideal sinusoidal current waveform. As indicated in chart (a), a negative charge $-Q$ provided to the electrode 10 at a negative part of the sinusoidal waveform corresponds to a positive charge $+Q$ provided to the electrode 10 at a positive part of the sinusoidal waveform. Thus, as illustrated in chart (b) of FIG. 2, during a full period of the sinusoidal waveform, no charge accumulation occurs.

FIG. 2 shows in chart (c) a nonideal sinusoidal current waveform. As indicated in chart (c), a negative charge $-Q$ provided to the electrode 10 at a negative part of the sinusoidal waveform is smaller than a positive charge $+Q$ provided to the electrode 10 at a positive part of the sinusoidal waveform. Thus, as illustrated in chart (d) of FIG. 2, a net charge accumulation will occur during a full period of the sinusoidal waveform. This implies that if the stimulation signal is provided continuously for a period of time a large charge accumulation may occur.

Referring again to FIG. 1, the stimulator circuit 100 further comprises a compensation unit 140. The compensation unit 140 may be connected between the stimulation signal generating unit 110 and the output 130 of the stimulator circuit 100. The compensation unit 140 may form a feedback loop for performing charge balancing during output of the stimulation signal by the stimulation signal generating unit 100 to the output 130.

The compensation unit 140 may thus be configured to provide a compensation current signal to the output 130 for compensating an unbalanced charge of the stimulation signal. It should be realized that the compensation unit 140 may not necessarily perfectly balance charge accumulation at the output 130 but may at least reduce charge accumulation so as to avoid risks involved with large offset voltage build-up at the electrode 10.

The compensation unit 140 may be configured to regulate a common mode voltage of the AC signal at the output 130 of the stimulator circuit 100. As illustrated in FIG. 1, the output 130 may be connected to tissue of a living being via the electrode 10 such that a current signal from the stimulation signal generating unit 110 is converted to a voltage signal. The common mode voltage may be thus be based on the stimulation signal.

The compensation unit 140 comprises a common mode voltage monitoring element 144, which is configured to monitor the common mode voltage at the output 130. The common mode voltage monitoring element 144 may thus be connected to receive a signal of the output 130 of the stimulator circuit 100.

The compensation unit 144 further comprises a charge balancing element 152 which may be configured to generate the compensation current signal based on the common mode voltage monitored by the common mode voltage monitoring element 144. The compensation unit 140 may be configured to output the compensation current signal to the output 130 of the stimulator circuit 100 for forming a compensated stimulation signal at the output 130.

Figure 3:
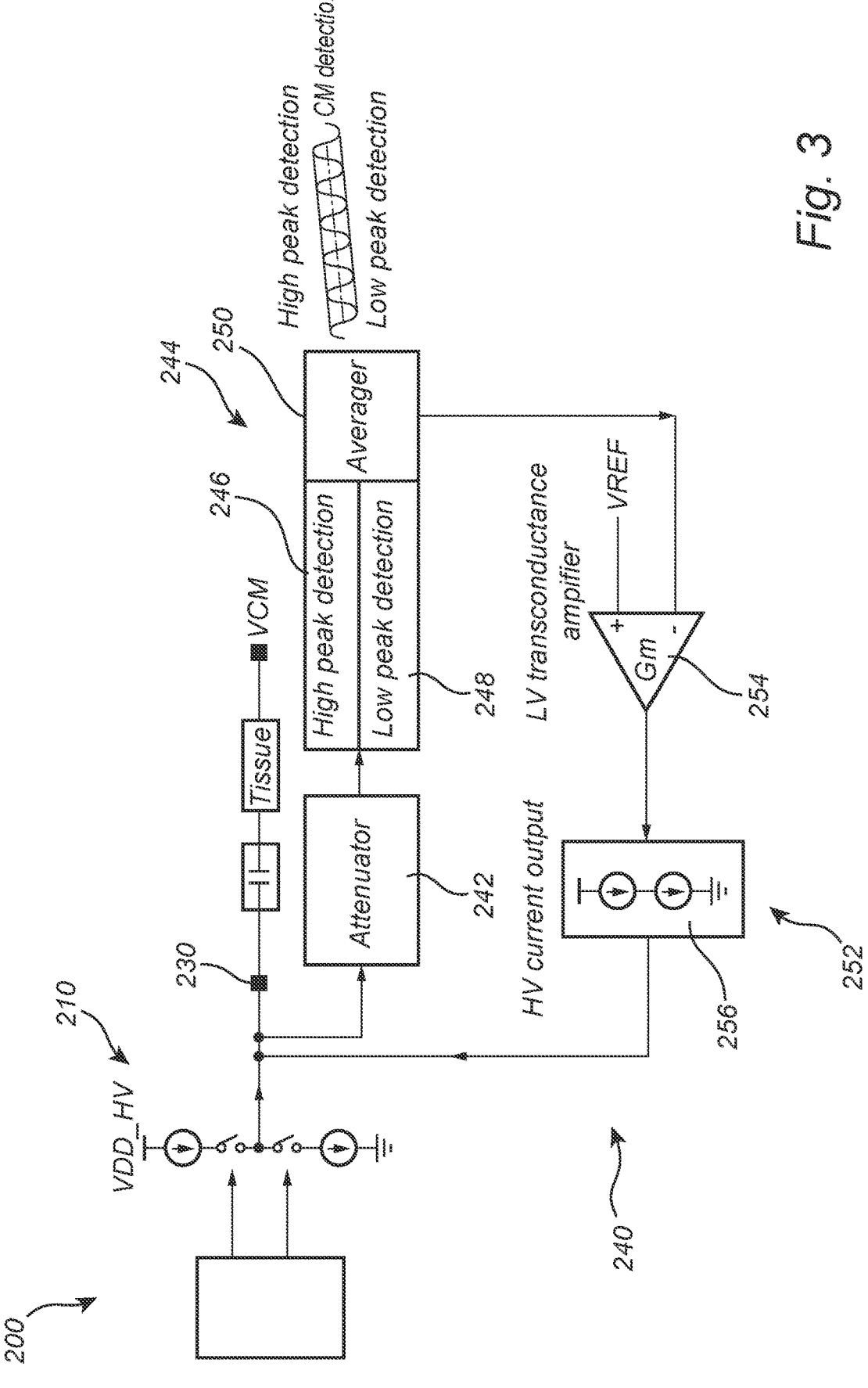
FIG. 3 is a schematic view of a stimulator circuit according to a second embodiment.

Referring now to FIG. 3, a stimulator circuit 200 according to a second embodiment will be described.

The stimulator circuit 200 is particularly adapted for use in applications where a large signal swing at the output 230 of the stimulator circuit 200 is desired. For instance, in peripheral nerve stimulation, the signal swing at the output 230 may preferably be in a range of tens of volts. The stimulation signal generating unit 210 may thus be implemented with a high voltage supply, such as 20 V supply voltage, to provide compliance of the stimulation signal generating unit 210 with large signal swings at the output 230.

The stimulation current provided by the stimulation signal generating unit 210 may be up to a few mA. This may imply that the compensation unit 240 may have a large power consumption.

In order for power consumption of the compensation unit 240 to be limited, the compensation unit may thus comprise an attenuator 242, the common mode monitoring element 244 operating at low voltage supply, a transconductance amplifier 254 of the charge balancing element 252 operating at low voltage supply and a current output stage 256 compatible with a high voltage signal swing.

Thus, it is realized that high voltage supply is not necessary for determining a feedback current for compensating an unbalanced charge. The attenuator 242 may be configured to attenuate the high voltage signal at the output 230 of the stimulator circuit 200. The common mode voltage monitoring element 244 may then be configured to monitor the common mode voltage based on an attenuated signal received from the attenuator 242.

The attenuator 242 may be configured to attenuate a received signal by a factor F to allow a lower supply voltage to be used in components processing the attenuated signal.

The attenuator 242 may be a passive component (such as a resistor/capacitor divider) or an active component.

The common mode voltage monitoring element 244 may be configured to provide common mode voltage monitoring using a low voltage supply. The common mode voltage monitoring element 244 may for example comprise a low pass filter for providing monitoring of the common mode voltage.

However, the offset voltage at the output 230 may change very slowly compared to frequency of the sinusoidal waveform. Thus, filtering of the sinusoidal signal may be performed by a high-order or low cut-off frequency filter. Thus, use of a low pass filter may be area consuming. Also, a design of the low pass filter may be complex if a signal swing of the input sinusoidal signal received by the common mode voltage monitoring element 244 goes rail-to-rail.

As shown in FIG. 3, the common mode voltage monitoring element 244 may be configured to perform extreme point detection of the input signal for determining an unbalance of the common mode voltage. The common mode voltage monitoring element 244 may comprise a maximum point detection element 246 and a minimum point detection element 248 for detecting local maxima and local minima of the input signal. The common mode voltage monitoring element 244 may further comprise an averaging element 250 for determining an average of the input signal based on the detected local maxima and detected local minima. The averaging element 250 may thus output a representation of the common mode voltage.

The charge balancing element 252 may be configured to receive a representation of the common mode voltage from the common mode monitoring element 244. The charge balancing element 252 may comprise a transconductance amplifier 254 which may also operate at low voltage supply for generating a feedback current based on which the compensation current signal may be generated.

The transconductance amplifier 254 may compare the received common mode voltage from the common mode voltage monitoring element 244 to a reference voltage. The transconductance amplifier 254 may be configured to generate the feedback current based on a voltage difference between the common mode voltage and the reference voltage.

The transconductance amplifier 254 may need a high transconductance Gm to provide good compensation based on the voltage difference. Thanks to the transconductance amplifier 254 being operated at low voltage supply, power consumption of the transconductance amplifier 254 may still be limited.

The feedback current from the transconductance amplifier 254 may further be provided to a current output stage 256 of the charge balancing element 252. The current output stage 256 may be configured to mirror or further amplify the feedback current. The current output stage 256 may thus further boost the transconductance Gm using an amplification A, such that the voltage difference detected by the transconductance amplifier 252 may be amplified by A*Gm.

The current output stage 256 may be implemented with a high voltage supply and provide a high output impedance. This implies that the compensation current signal output by the current output stage 256 to the output 230 of the stimulator circuit 200 may be compatible with a large signal swing at the output 230.

An offset voltage at the output 230 of the stimulator circuit 200 may after compensation be proportional to $I_{mismatch}*F/(A*Gm)$, where $I_{mismatch}$ is a current corresponding to mismatch in charges provided to the electrode 10 at the positive and negative parts of the stimulation signal from the stimulation signal generating unit 210. Thus, if the term A*Gm is increased, the offset voltage at the output 230 is decreased.

The compensation unit 240 may be configured to output the compensation current signal as a DC signal. If compensation loop formed by the compensation unit 240 is stable, the compensation current signal will be a DC current. This implies that the compensation current signal may not affect the stimulation provided to the living being. In particular, if the stimulation is to be provided as an interferential stimulation based on interference between two or more stimulation signals, the interference is dependent on frequency of the stimulation signals and a DC signal will not affect the interferential signal. Also, the compensation current is usually a small DC current, such as 1% of 10 mA or 10% of 1 mA, depending on the mismatch. This also implies that the compensation current signal will not affect the stimulation.

The compensation unit 240 may be configured to be duty cycled. Thus, the compensation unit 240 may be configured to receive a control signal for activating and de-activating the compensation unit 240. Thus, power consumption of the stimulator circuit 200 may be reduced by the compensation unit 240 not being continuously active.

The compensation current signal may thus be a discrete time compensation current, and the compensation current signal may be provided during the time periods when the compensation unit 240 is active.

Figures 4, 5:
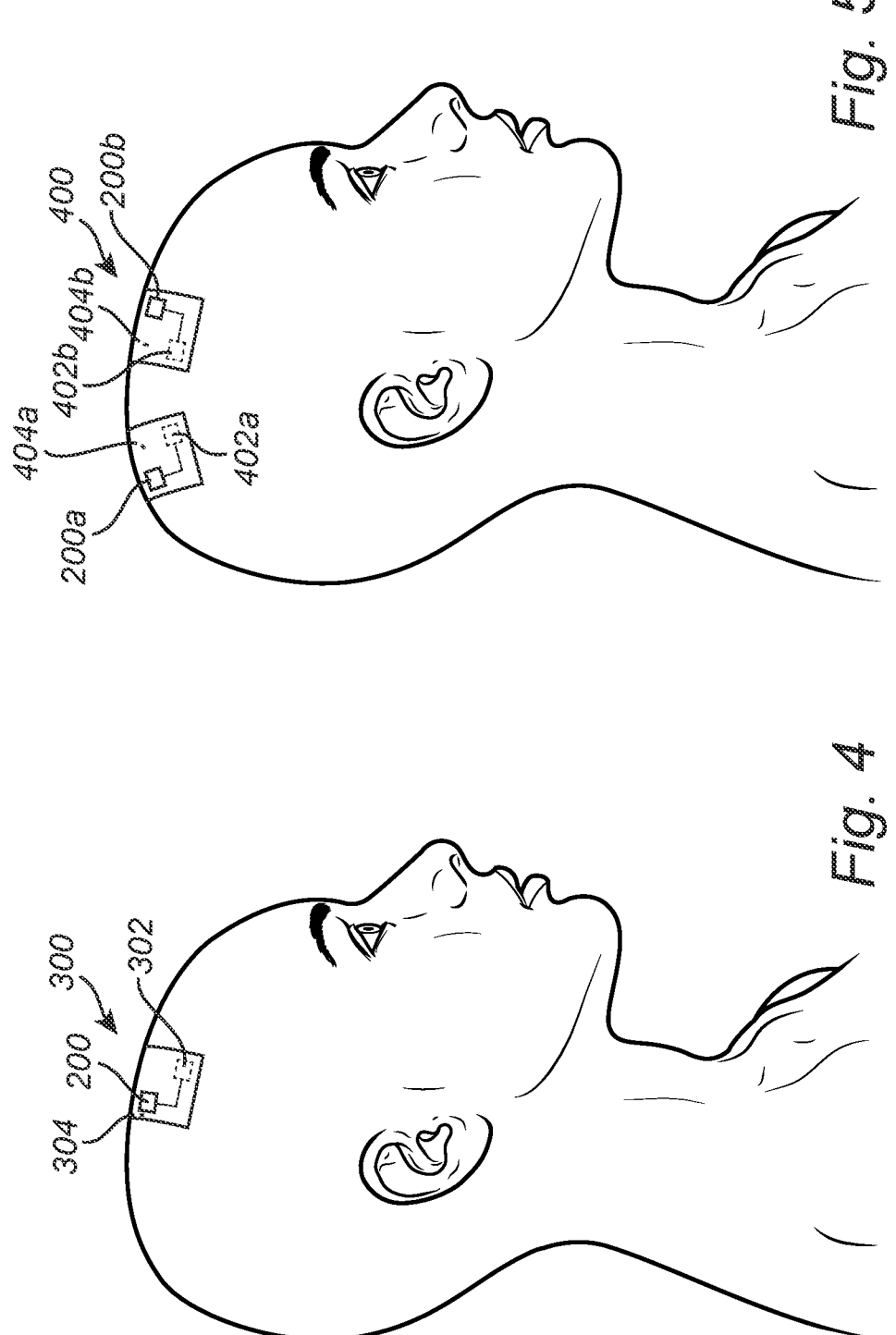
FIG. 4 is a schematic view of a system according to an embodiment.
FIG. 5 is a schematic view of a system according to another embodiment.

Referring now to FIG. 4, a system 300 for providing stimulation to a living being will be described. The system 300 is shown to provide stimulation of a brain. However, it should be realized that the system 300 may alternatively provide stimulation of a nerve, such as a peripheral nerve.

The system 300 comprises the stimulator circuit 200. It should be realized that the system 300 may comprise any variant of stimulator circuit described above. The system 300 further comprises at least one electrode 302 connected to the output 230 of the stimulator circuit 200.

The at least one electrode 302 may be arranged in or on a carrier 304 adapted to be arranged in relation to the living being, such as being arranged in relation to the brain so as to define a desired relation between the at least one electrode 302 and the brain. The stimulator circuit 200 may also be arranged in the carrier 304, which may facilitate arranging the system 300 on a living being when stimulation is to be provided. However, it should be realized that the stimulator circuit 200 may alternatively be provided in a separate housing from the at least one electrode 302 and the at least one electrode 302 may be connected to the stimulator circuit 200 using wires.

The at least one electrode 302 may be configured to transmit the compensated stimulation signal from the stimulator circuit 200 into the brain of the living being. It should be realized that the stimulation signal may be provided into the brain of the living being based on use of a pair of electrodes. However, the system 300 may comprise only one electrode configured to receive the compensated stimulation signal, whereas another electrode in the pair of electrodes may be a reference electrode, which may be separate from the system 300 and which may be shared by a plurality of stimulator circuits 200.

Referring now to FIG. 5, a system 400 for providing stimulation to a living being will be described. The system 400 is shown to provide stimulation of a brain. However, it should be realized that the system 400 may alternatively provide stimulation of a nerve, such as a peripheral nerve.

The system 400 comprises a first stimulator circuit 200a and a second stimulator circuit 200b. Each of the first stimulator circuit 200a and the second stimulator circuit 200b may be any variant of stimulator circuit described above. The system 400 further comprises at least one first electrode 402a connected to the output of the first stimulator circuit 200a and at least one second electrode 402b connected to the output of the second stimulator circuit 200b.

The at least one first electrode 402a and the at least one second electrode 402b may be arranged in or on a common carrier adapted to be arranged in relation to the living being, such as being arranged in relation to the brain so as to define a desired relation between the respective electrode 402a, 402b and the brain. The first and second stimulator circuits 200a, 200b may also be arranged in the common carrier. However, according to an alternative, as shown in FIG. 5, the at least one first electrode 402a may be arranged in or on a first carrier 404a and the first stimulator circuit 200a may also be arranged in the first carrier 404a. Further, the at least one second electrode 402b may be arranged in or on a second carrier 404b and the second stimulator circuit 200b may also be arranged in the second carrier 404b. This may allow larger flexibility in arranging the electrodes in relation to the brain.

Further, it should be realized that the stimulator circuits 200a, 200b may alternatively be provided in separate housing(s) from the at least one first electrode 402a and the at least one second electrode 402b. The at least one first electrode 402a and the at least one second electrode 402b may be connected to the first stimulator circuit 200a and the second stimulator circuit 200b, respectively, using wires.

The at least one first electrode 402a may be configured to transmit the compensated stimulation signal from the stimulator circuit 200a into the brain of the living being. It should be realized that the stimulation signal may be provided into the brain of the living being based on use of a pair of electrodes. However, the system 400 may comprise only one first electrode 402a configured to receive the compensated stimulation signal, whereas another electrode in the pair of electrodes may be a reference electrode, which may be separate from the system 400. Similarly, the at least one second electrode 402b may be configured to transmit the compensated stimulation signal from the stimulator circuit 200b into the brain of the living being. It should be realized that the stimulation signal may be provided into the brain of the living being based on use of a pair of electrodes. However, the system 400 may comprise only one second electrode 402b configured to receive the compensated stimulation signal, whereas another electrode in the pair of electrodes may be a reference electrode, which may be separate from the system 400. The reference electrode may be shared for output of the compensated stimulation signals from both the first stimulator circuit 200a and the second stimulator circuit 200b to the first electrode 402a and the second electrode 402b in relation to the shared reference electrode.

The at least one first electrode 402a and the at least one second electrode 402b may be configured to be arranged in relation to the brain such that the first compensated stimulation signal and the second compensated stimulation signal transmitted into the brain may form an interferential stimulation signal in the brain based on interference between the first and the second compensated stimulation signal. The system 400 may thus be configured to provide stimulation of the brain by the interferential stimulation signal.

The system 400 may further comprise a control unit configured to control the first and second stimulator circuits 200a, 200b such that the first compensated stimulation signal and the second compensated stimulation signal have a desired relation, e.g., being synchronized, in order to form a desired interferential stimulation signal in the brain.

Figure 6:
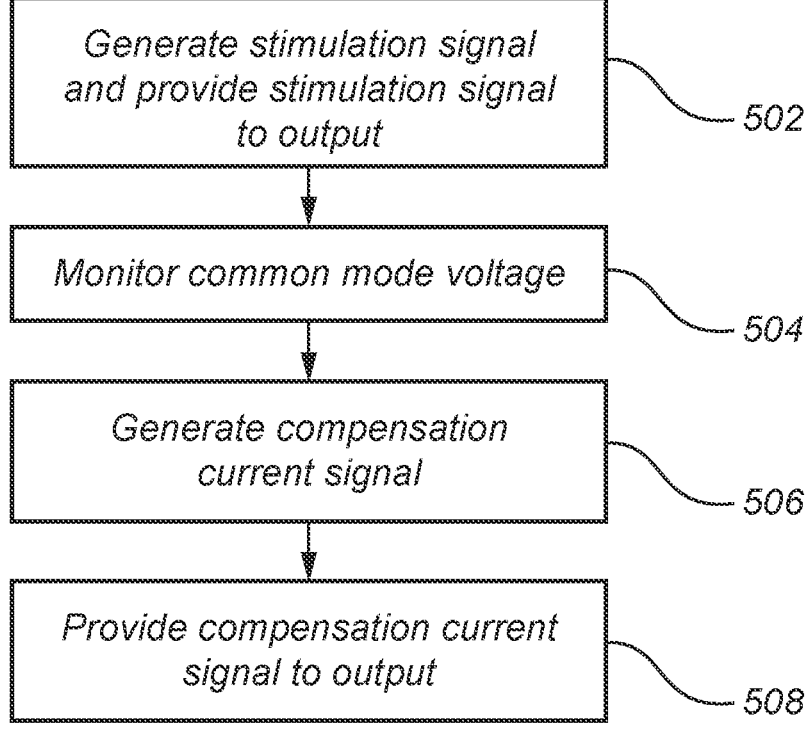
FIG. 6 is a flow chart of a method.

Referring now to FIG. 6, a method for providing a compensated stimulation signal will be described.

The method comprises generating 502 a stimulation signal and providing the stimulation signal to an output. The stimulation signal is an AC signal having a sinusoidal-like waveform. The output may be connected to an electrode configured to transmit a received signal for stimulation of a brain and/or a nerve of a living being.

The method further comprises monitoring 504 a common mode voltage based on the stimulation signal, generating 506 a compensation current signal based on the common mode voltage and providing 508 the compensation current signal to the output.

The monitoring of the common mode voltage may allow identifying of an unbalanced charge being provided to the output based on the stimulation signal. Thus, the compensation current signal may be generated in dependence of the monitoring of the common mode voltage for compensating an unbalanced charge of the stimulation signal. The compensation current signal being provided to the output implies that the compensated stimulation signal is formed at the output.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A stimulator circuit, said stimulator circuit comprising:
   a stimulation signal generating unit configured to generate a stimulation signal and provide the stimulation signal to an output, wherein the stimulation signal is an alternating current (AC) signal having a sinusoidal-like waveform; and
   a compensation unit configured to generate a compensation current signal, wherein the compensation unit comprises a common mode voltage monitoring element configured to monitor a common mode voltage based on the stimulation signal, and a charge balancing element configured to generate the compensation current signal based on the common mode voltage;

wherein the compensation unit is configured to provide the compensation current signal to the output for compensating an unbalanced charge of the stimulation signal and forming a compensated stimulation signal at the output.

2. The stimulator circuit according to claim 1, wherein the compensation unit is configured to generate the compensation current signal during the stimulation signal being provided to the output by the stimulation signal generating unit.

3. The stimulator circuit according to claim 1, wherein the common mode voltage monitoring element is configured to perform extreme point detection of the stimulation signal for determining an unbalance of the common mode voltage based on the stimulation signal.

4. The stimulator circuit according to claim 3, wherein the common mode voltage monitoring element comprises a maximum point detection element for detecting local maxima of the stimulation signal, a minimum point detection element for detecting local minima of the stimulation signal, and an averaging element for determining an average based on detected local maxima and detected local minima for monitoring the common mode voltage.

5. The stimulator circuit according to claim 1, wherein the compensation unit comprises an attenuator configured to attenuate the stimulation signal, and wherein the common mode voltage monitoring element is configured to monitor the common mode voltage based on an attenuated stimulation signal received from the attenuator.

6. The stimulator circuit according to claim 5, wherein the compensation unit further comprises a transconductance amplifier for generating a feedback current based on comparing the common mode voltage to a reference voltage.

7. The stimulator according to claim 6, wherein the compensation unit further comprises a current output stage configured to amplify the feedback current for forming the compensation current signal.

8. The stimulator circuit according to claim 1, wherein the compensation unit is configured to be duty cycled.

9. The stimulator circuit according to claim 1, wherein the compensation current signal is a direct current (DC) signal.

10. The stimulator circuit according to claim 1, wherein the stimulation signal generating unit comprises a current source and a current sink for generating the AC stimulation signal, wherein the current source and the current sink are independent components.

11. A system for providing stimulation of a brain and/or a nerve of a living being, said system comprising:
the stimulator circuit according to claim 1; and
at least one electrode connected to the stimulator circuit for receiving the compensated stimulation signal from the output of the stimulator circuit, wherein the at least one electrode is configured to be arranged in relation to the brain and/or the nerve for transmitting the compensated stimulation signal into the brain and/or the nerve.

12. A system for providing temporal interference stimulation of a brain and/or a nerve of a living being, said system comprising:
a first stimulator circuit according to claim 1 for forming a first compensated stimulation signal at the output of the first stimulator circuit;
at least one first electrode connected to the first stimulator circuit for receiving the first compensated stimulation signal from the output of the first stimulator circuit, wherein the at least one first electrode is configured to be arranged in a first relation to the brain and/or the nerve for transmitting the first compensated stimulation signal into the brain and/or the nerve;
a second stimulator circuit for forming a second compensated stimulation signal at the output of the second stimulator circuit, wherein the second stimulator circuit comprises a stimulation signal generating unit configured to generate a stimulation signal and provide the stimulation signal to an output, wherein the stimulation signal is an alternating current (AC) signal having a sinusoidal-like waveform; and a compensation unit configured to generate a compensation current signal, wherein the compensation unit comprises a common mode voltage monitoring element configured to monitor a common mode voltage based on the stimulation signal, and a charge balancing element configured to generate the compensation current signal based on the common mode voltage;
wherein the compensation unit is configured to provide the compensation current signal to the output for compensating an unbalanced charge of the stimulation signal and forming a compensated stimulation signal at the output; and
at least one second electrode connected to the second stimulator circuit for receiving the second compensated stimulation signal from the output of the second stimulator circuit, wherein the at least one second electrode is configured to be arranged in a second relation to the brain and/or the nerve for transmitting the second compensated stimulation signal into the brain and/or the nerve;
wherein the at least one first electrode and the at least one second electrode are configured to be arranged in relation to the brain and/or the nerve for forming an interferential stimulation signal in the brain and/or the nerve based on interference between the first compensated stimulation signal and the second compensated stimulation signal.

13. A method for providing a compensated stimulation signal in a stimulator circuit according to claim 1, said method comprising:
generating a stimulation signal and providing the stimulation signal to an output, wherein the stimulation signal is an alternating current (AC) signal having a sinusoidal-like waveform;
monitoring a common mode voltage based on the stimulation signal;
generating a compensation current signal based on the common mode voltage and providing the compensation current signal to the output for compensating an unbalanced charge of the stimulation signal and forming the compensated stimulation signal at the output.

14. A method for providing a compensated stimulation signal in a system according to claim 11, said method comprising:
generating a stimulation signal and providing the stimulation signal to an output, wherein the stimulation signal is an alternating current (AC) signal having a sinusoidal-like waveform;
monitoring a common mode voltage based on the stimulation signal;
generating a compensation current signal based on the common mode voltage and providing the compensation current signal to the output for compensating an unbalanced charge of the stimulation signal and forming the compensated stimulation signal at the output.

\* \* \* \* \*